United States Patent
Smarrito-Menozzi et al.

(10) Patent No.: US 10,781,232 B2
(45) Date of Patent: *Sep. 22, 2020

(54) SUGAR-DIPEPTIDE CONJUGATES AS FLAVOR MOLECULES

(71) Applicant: NESTEC S.A., Vevey (CH)

(72) Inventors: Candice Marie Smarrito-Menozzi, Belmont-sur-Lausanne (CH); Florian Viton, Lausanne (CH); Thomas Hofmann, Neufahrn (DE); Maximilian Kranz, Freising (DE)

(73) Assignee: Societe des Produits Nestle S.A., Vevey (CH)

( * ) Notice: Subject to any disclaimer, the term of this patent is extended or adjusted under 35 U.S.C. 154(b) by 234 days.

This patent is subject to a terminal disclaimer.

(21) Appl. No.: 15/546,182

(22) PCT Filed: Jan. 26, 2016

(86) PCT No.: PCT/EP2016/051543
§ 371 (c)(1),
(2) Date: Jul. 25, 2017

(87) PCT Pub. No.: WO2016/120257
PCT Pub. Date: Aug. 4, 2016

(65) Prior Publication Data
US 2019/0119319 A1   Apr. 25, 2019

(30) Foreign Application Priority Data

Jan. 30, 2015 (EP) .................................. 15153288

(51) Int. Cl.
| | | |
|---|---|---|
| *C07K 5/062* | (2006.01) | |
| *A23L 27/23* | (2016.01) | |
| *A23L 23/00* | (2016.01) | |
| *C07H 7/06* | (2006.01) | |
| *A23L 27/00* | (2016.01) | |

(52) U.S. Cl.
CPC .......... *C07K 5/06026* (2013.01); *A23L 23/00* (2016.08); *A23L 27/23* (2016.08); *A23L 27/88* (2016.08); *C07H 7/06* (2013.01)

(58) Field of Classification Search
CPC ...... C07K 5/06026; C07H 15/26; C07H 7/02; A23L 23/10; A23L 23/00; A23L 27/23; A23L 27/88; A23L 27/215; A23L 27/21
See application file for complete search history.

(56) References Cited

FOREIGN PATENT DOCUMENTS

EP    1252825    10/2002

OTHER PUBLICATIONS

Lowy, P.H., Borsook, H. 1956. "Preparation of N-substituted 1-Amino-1-deoxy-D-arabino-hexuloses of Arginine, Histidine and Lysine." J. Am. Chem. Soc., vol. 78, pp. 3175-3176.*
Mossine, V.V., Mawhinney, T.P. 2007. "Nα-(1-Deoxy-D-fructos-1-yl)-L-histidine ("D-Fructose-L-histidine"): a Potent Copper Chelator from Tomato Powder." J. Agric. Food Chem., vol. 55, pp. 10373-10381.*
Ryu, K., Ide, N., Matsurra, H., Itakura, Y. 2001. "Nα-(1-Deoxy-D-fructos-1-yl)-L-Arginine, an Antioxidant Compound Identified in Aged Garlic Extract." J. Nut. vol. 131, pp. 972S-976S.*
Seifert, S.T., Krause, R., Gloe, K., Henle, T. 2004. "Metal Complexation by the Peptide-Bound Maillard Reaction Products Nε-Fructoselysine and Nε-Carboxymethyllysine." J. Agric. Food Chem. vol. 52, pp. 2347-2350.*
Sonntag et al. "Sensory-Guided Identification of N-(1-Methyl-4-oxoimidazolidin-2-ylidene)-α-amino Acids as Contributors to the Thick-Sour arid Mouth-Drying Orosensation of Stewed Beef Juice" Journal of Agricultural and Food Chemistry, 2010, vol. 58, pp. 6341-6350.
Dunkel et al. "Sensory-Directed Identification of β-Alanyl Dipeptides as Contributors to the Thick-Sour and White-Meaty Orosensation Induced by Chicken Broth" Journal of Agricultural and Food Chemistry, 2009, vol. 57, pp. 9867-9877.

* cited by examiner

*Primary Examiner* — Nikki H. Dees
(74) *Attorney, Agent, or Firm* — K&L Gates LLP

(57) ABSTRACT

The present invention relates to compounds and compositions for use in enhancing flavor and umami taste of food products. Particularly, the present invention relates to compounds of the general formula I) and compositions comprising them.

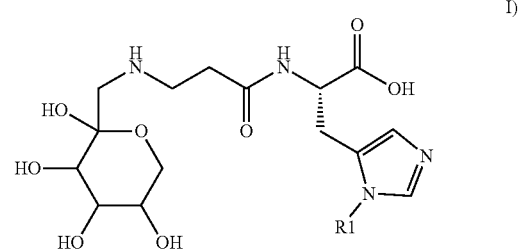

8 Claims, 2 Drawing Sheets

SUGAR-DIPEPTIDE CONJUGATES AS FLAVOR MOLECULES

CROSS REFERENCE TO RELATED APPLICATIONS

The present application is a National Stage of International Application No. PCT/EP2016/051543, filed on Jan. 26, 2016, which claims priority to European Patent Application No. 15153288.4, filed on Jan. 30, 2015, the entire contents of which are being incorporated herein by reference.

The present invention relates to compounds and compositions for use in enhancing flavor and umami taste of food products.

Many foods that are consumed today are rich in umami taste. Umami represents the taste of the amino acid L-glutamate and 5'-ribonucleotides such as guanosine 5'-monophosphate (GMP) and 5'-inosine monophosphate (IMP) and is sometimes also called the fifth taste. The word umami derives from the Japanese for delicious and the umami taste can be described as "savoury", "brothy" or "meaty" taste. The sensation of umami is due to the activation of taste receptor cells assembled into taste buds, distributed across different papillae of the tongue and the palate epithelium (Chandrashekar et al., 2006, Nature, 444, 288-294). Its effect is to balance taste and round out the overall flavor of a dish. Furthermore, umami enhances the palatability of a wide variety of food products. Naturally occurring glutamate can be found for example in many meat and vegetable food preparations (Ghirri et al., 2012, International Journal of Food Sciences and Nutrition, 63(7), 872-881.).

Umami or savoury, meaty taste of a food product can be further achieved and/or enhanced by adding separately monosodium glutamate (MSG) and/or the ribonucleotides GMP and IMP into those culinary recipes. Many taste enhancers comprising such MSG and/or ribonucleotides have been developed by the food industry and are available world-wide in the trade. A wide variety of ready-to-use taste enhancers are therefore available for various different culinary applications and in various different forms such as pastes, powders, liquids, compressed cubes or granules.

The addition of those culinary additives helps to provide deliciousness and enhanced taste appealing properties to food products to which they were added. Indeed, all around the world, deliciousness and appealing taste is perceived as one of the key attributes of a high quality meal. However, in many parts of the world, the addition of MSG and/or ribonucleotides has received bad press and is more and more negatively perceived by consumers. Although MSG and those ribonucleotides are naturally occurring in many food products, such as in tomatoes and meat products, and have been proven to be safe by several organizations including the World Health Organisation (WHO) and the European Food Safety Authority (EFSA), a publication in the New England Journal of Medicine (Kwok, R H M, 1968 New England Journal of Medicine, 278 (14), 796) sparked speculation among consumers about detrimental effects of MSG and ribonucleotides leading many consumers to reject products containing large amounts of such added compounds. There is therefore a strong need for industrial solutions allowing reducing the use of added MSG and ribonucleotides to food or taste enhancing products, without however compromising on umami taste and still ensuring savory superiority of such culinary products.

For example, in a recent scientific publication from A. Dunkel and T. Hofmann (Dunkel and Hofmann, 2009, J. Agric. Food Chem. 2009, 57, 9867-9877), sensory-directed fractionation of a freshly prepared double-boiled chicken soup led to the identification of the β-alanyl dipeptides L-anserine, L-carnosine and β-alanylglycine as contributors to the thick-sour and white-meaty orosensation. Quantitative analysis, followed by taste recombination and omission experiments, revealed for the first time that, when present together with L-glutamic acid and sodium and/or potassium ions, sub-threshold concentrations of these three β-alanyl peptides enhance the typical thick-sour orosensation and white-meaty character known for poultry meat. This is a first step in finding new compounds which are able to impart flavour richness and enhance the umami taste effect of MSG, and thereby allowing a reduced use of MSG.

The object of the present invention is to improve the state of the art and to provide an alternative or improved solution to the prior art to overcome at least some of the inconveniences described above. Particularly, the object of the present invention is to provide an alternative or improved solution for enhancing the flavour and/or umami taste of a food product.

The object of the present invention is achieved by the subject matter of the independent claims. The dependent claims further develop the idea of the present invention.

Accordingly, the present invention provides in a first aspect a compound of the general formula I,

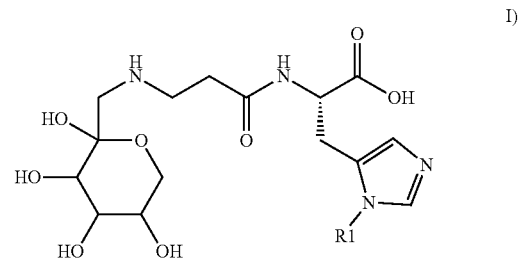

wherein R1 is a hydrogen, a $C_1$, a $C_2$, a $C_3$, or a $C_4$ alkyl group; or a salt of said compound.

In a second aspect, the invention relates to a composition comprising said compound of the general formula I) in an amount of at least 1 mg/g, at least 1.7 mg/g, at least 2 mg/g, at least 2.5 mg/g, at least 3 mg/g, at least 3.5 mg/g, or at least 5 mg/g of the total composition.

Further aspects of the present invention relate to a use of said compound for enhancing the flavor and/or the umami taste of a food product.

Still further aspects of the present invention relate to a use of a composition comprising said compound in an amount of at least 1 mg/g, at least 1.7 mg/g, at least 2 mg/g, at least 2.5 mg/g, at least 3 mg/g, at least 3.5 mg/g, or at least 5 mg/g, for enhancing the flavor and/or the umami taste of a food product.

A still further aspect of the present invention is a method for enhancing the flavor and/or umami taste of a culinary food product, comprising the step of adding said compound or the composition comprising said compound to a food product.

The inventors surprisingly found that some sugar conjugates of β-alanyl dipeptides have a much stronger flavor enhancing effect than their corresponding aglycones. In fact, these sugar conjugates enhance umami perception and induce a thick-sour and white meaty orosensation of a culinary recipe at much lower threshold levels than their corresponding aglycones. The sugar-β-alanyl dipeptide molecules are typically generated in-situ during thermal processing of food raw materials by condensation of glucose with β-alanyl-dipeptides such as e.g. carnosine and anserine. For example, these molecules have been identified by the inventors in a traditional soup dish such as pot-au-feu in concentrations of about 7-10 μmol/L, which corresponds to about 2.7 to 3.9 μg/g. The corresponding aglycones, i.e. the β-alanyl dipeptides, have been identified for example in stewed beef juice or in chicken broth and have been previously described as inducing thick-sour and mouth-drying orosensation (Sonntag et al., 2010, J. Agric. Food Chem. 58, 6341-6350; Dunkel et al., 2009, J. Agric. Food Chem., 57, 9867-9877). However, the taste enhancing threshold levels of these specific β-alanyl dipeptides are much higher than the ones of their corresponding sugar conjugates. Evidence thereof is provided in the Example section below. Therefore, the molecules described in the present invention are more potent flavor and umami taste enhancers than the known β-alanyl dipeptides. They allow further reducing the amounts and uses of MSG and/or ribonucleotides in culinary food products without compromising flavor richness and/or reducing the typical and well desired umami taste of said products. They also allow generating umami savory food concentrates which have much less or no MSG and/or ribonucleotides and still provide a strong and typical umami taste if applied to a food product. It even allows generating such umami savory food concentrates which are much stronger and more concentrated in providing an umami taste to a food product upon application.

DETAILED DESCRIPTION OF THE INVENTION

Figure 1:
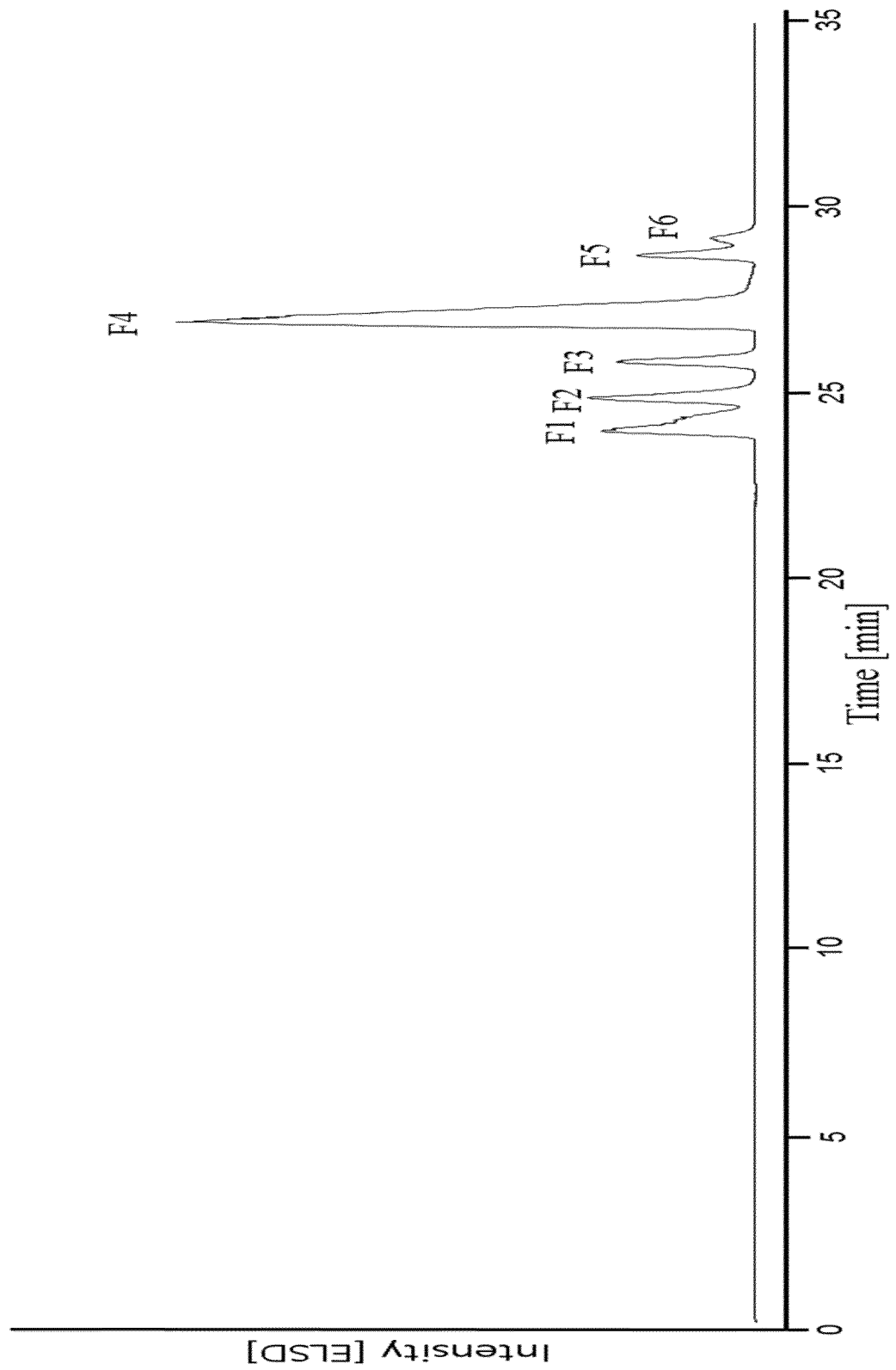
FIG. 1: HPLC-UV chromatogram of a thermally treated carnosine with glucose.

The present invention pertains to a compound of the general formula I), wherein R1 is a hydrogen, a $C_1$, a $C_2$, a $C_3$, or a $C_4$ alkyl group; or a salt of said compound. In one embodiment, the R1 group of the compound of the present invention is a hydrogen or a methyl group. The chemical names of those corresponding two compounds are: 1-deoxy-D-fructosyl-N-β-alanyl-L-histidine and 1-deoxy-D-fructosyl-N-β-alanyl-N-methyl-L-histidine, respectively.

A second aspect of the invention relates to a composition comprising said compound of the general formula I) in an amount of at least 1 mg/g, at least 1.7 mg/g, at least 2 mg/g, at least 2.5 mg/g, at least 3 mg/g, at least 3.5 mg/g, or at least 5 mg/g of the total composition.

In one embodiment, the composition of the present invention is an extract from plant and/or meat material. For example, the composition is an extract from beef meat, chicken meat, pork meat or a combination thereof.

In another embodiment, the composition of the present invention is the result of a flavor reaction. The term "flavor reaction" refers herein to a chemical reaction occurring between at least one reducing sugar and at least one amino acid or protein. Typically, this chemical reaction occurs during a heating process and is typically also referred to as Maillard reaction. In one example, the flavor reaction is a Maillard reaction.

In a preferred embodiment, the composition of the present invention is food grade. Under "food grade" the inventors mean that the composition is suitable for human consumption, for example directly, in concentrated form, and/or when used diluted in a food product.

For example, the composition of the present invention is selected from the group consisting of a culinary seasoning product, a cooking aid, a sauce or soup concentrate, a dry or wet pet-food product.

Further aspects of the present invention relate to a use of said compound for enhancing the flavor and/or the umami taste of a food product. Such a food product may be a ready-to-eat food product. It may also be a flavor concentrate used for seasoning a still further other food product. Advantageously, the compound of the present invention may be used for being added to a seasoning, a cooking aid or a food concentrate product. Thereby the strength of providing an umami taste to a still further food product is improved in such a seasoning, cooking aid or food concentrate product.

Further aspects of the present invention also relate to a use of a composition comprising said compound in an amount of at least 1 mg/g, at least 1.7 mg/g, at least 2 mg/g, at least 2.5 mg/g, at least 3 mg/g, at least 3.5 mg/g, or at least 5 mg/g of the total composition, for enhancing the flavor and/or the umami taste of a food product. Advantageously, such a food product may be a ready-to-eat food product. The use of the present invention has the advantage that it allows to use natural extracts which for example have been enriched in said compounds for flavoring and improving the natural umami taste of those food products.

A still further aspect of the present invention is a method for enhancing the flavor and/or umami taste of a culinary food product, comprising the step of adding said compound or the composition comprising said compound to a food product. The food product can be a ready-to-eat food product or a flavor concentrate.

As an example of the present invention, the final concentration of said compound in the food product is at least 1 mg/g, at least 1.7 mg/g, at least 2 mg/g, at least 2.5 mg/g, at least 3 mg/g, at least 3.5 mg/g, or at least 5 mg/g of the composition. This advantageously, allows generating for example food seasoning products and flavor concentrate products which convey a strong umami taste to a further food product upon application.

Those skilled in the art will understand that they can freely combine all features of the present invention disclosed herein. In particular, features described for the products of the present invention may be combined with the uses and method of the present invention, and vice versa. Further, features described for different embodiments of the present invention may be combined.

Further advantages and features of the present invention are apparent from the figures and examples.

EXAMPLE 1

Synthesis of 1-deoxy-D-fructosyl-N-β-alanyl-L-histidine from Glucose and Carnosine (β-alanyl-L-histidine)

Chemicals: Sodium bisulphite and glycerol were purchased from Sigma, glucose from SDfine Chemicals, carnosine from ChemImprex, methanol and acetic acid from Merck. All commercially available reagents were used as received, from their respective suppliers.

Analytical thin layer chromatography (TLC) was carried out on RP-18 F254s (Merck) plates. The TLC plates were visualized by shortwave UV light, Ninhydrin stain.

$^1$H NMR (360.13 MHz) and $^{13}$C NMR (90.56 MHz) spectra were recorder on a Bruker DPX-360 spectrometer equipped with a broadband multinuclear z-gradient probehead. The chemical shifts (in ppm) were expressed with respect to an internal reference (TMS or TSP). Multiplicities are reported as follows: s=singlet, d=doublet, t=triplet, q=quadruplet, m=multiplet, bs=broad singlet.

D-Glucose (23 g, 127.37 mmol, 2.8 eq.) and sodium bisulfite (1.6 g, 12.389 mmol, 0.28 eq.) were suspended in methanol (38 mL) and glycerol (19 mL). After stirring for 30 min at 100° C., carnosine (10 g, 44.22 mmol, 1.0 eq.) and acetic acid (5.1 mL) were added and the resulting mixture was heated for 3.5 hours at 100° C. Reaction mass was then cooled down and diluted with 38 mL water. The reaction mixture was purified using a column packed in Amberlite IRN-77 ion exchange resin (100 g). $NH_3$ 0-0.4% was used as gradient in water for elution. Finally, 6.8 g 1-deoxy-D-fructosyl-N-β-alanyl-L-histidine were isolated (39.62%); Rf (n-Butanol:Acetic Acid:Water, 3:2:2): 0.21; MS (M$^+$): m/z 388.16; $^1$H NMR (Deuterium Oxide) δ 2.77 [m, 2H], 3.13 [dd, J=15.4, 8.2 Hz, 1H], 3.21-3.27 [m, 1H], 3.28-3.32 [m, 2H], 3.33-3.44 [m, 2H], 3.63-3.75 [m, 1H], 3.76-3.85 [m, 2H], 3.87-3.91 [m, 1H], 3.99-4.03 [m, 2H], 4.53 [dd, J=8.2, 5.2 Hz, 1H], 7.28 [d, J=1.0 Hz, 1H], 8.61 [d, J=1.4 Hz, 1H]; $^{13}$C NMR (Deuterium Oxide) δ 26.98, 30.26, 44.28, 53.01, 53.92, 63.91, 68.80, 69.20, 69.76, 95.21, 116.65, 129.49, 133.15, 171.60, 176.13.

EXAMPLE 2

Preparation of 1-deoxy-D-fructosyl-N-β-alanyl-L-histidine from Glucose and Carnosine (β-alanyl-L-histidine)

A mixture of carnosine (226 mg; 1 mmol; 1 eq.) and glucose (360 mg; 2 mmol; 1 eq.) in 20 mL $Na_2HPO_4$ buffer (0.5 mol/L, pH 7.0) was heated in a closed vessel at 80° C. for 3 h. The solvent was then evaporated under reduced pressure and the resulting precipitate was freeze-dried. Aliquots of the freeze-dried powder were dissolved in water upon ultrasonification for 10 min and filtrated (0.45 μm). The solutions were then fractionated by a semi-preparative hydrophilic interaction liquid chromatography (HILIC-HPLC) using a 300×21.5 mm i.d., 10 μm, TSKgel Amide-80 column (Tosoh Bioscience, Stuttgart, Germany) equipped with a 75×21.5 i.d., 10 μm, guard column (Tosoh Bioscience, Stuttgart, Germany). Monitoring the effluent with an ELSD detector (Evaporative Light Scattering Detector) and adjusting the flow rate to 8 mL/min, a gradient consisting of aqueous formic acid (1% in water, solvent A) and acetonitrile (solvent B) was used. Starting with a mixture of 75% B and 25% A for 10 min, the gradient was reduced successively to 0% B and 80% A within another 10 min. After holding these conditions for 5 min, the gradient was increased to 75% B and 25% A within 8 min. The purification led to 6 fractions as shown in the FIG. 1.

The molecule corresponding to fraction F5 was identified as carnosine while the molecule F6 was identified as 1-deoxy-D-fructosyl-N-β-alanyl-L-histidine (based on LC-MS and NMR data).

EXAMPLE 3

Preparation of 1-deoxy-D-fructosyl-N-β-alanyl-L-histidine from Glucose and Carnosine (β-alanyl-L-histidine)

A mixture of carnosine (905 mg; 4 mmol) and potassium hydroxide (224 mg; 4 mmol) in 100 mL methanol was refluxed for 2 h. After cooling down to room temperature, the precipitate was removed by filtration and the supernatant was concentrated under reduced pressure leading to the carnosine potassium salt. Then, a mixture of the carnosine potassium salt (2 mmol) and glucose (360 mg; 2 mmol) in methanol (50 mL, pH 5.0 with formic acid) was heated at 80° C. in a closed vessel for 2 h. After evaporating the solvent under reduced pressure, the precipitate was dissolved in water and freeze-dried. The reaction product was purified using same conditions as reported in the Example 2.

EXAMPLE 4

Preparation of 1-deoxy-D-fructosyl-N-β-alanyl-N-methyl-L-histidine from Glucose and Anserine (β-alanyl-N-methyl-L-histidine)

Figure 2:
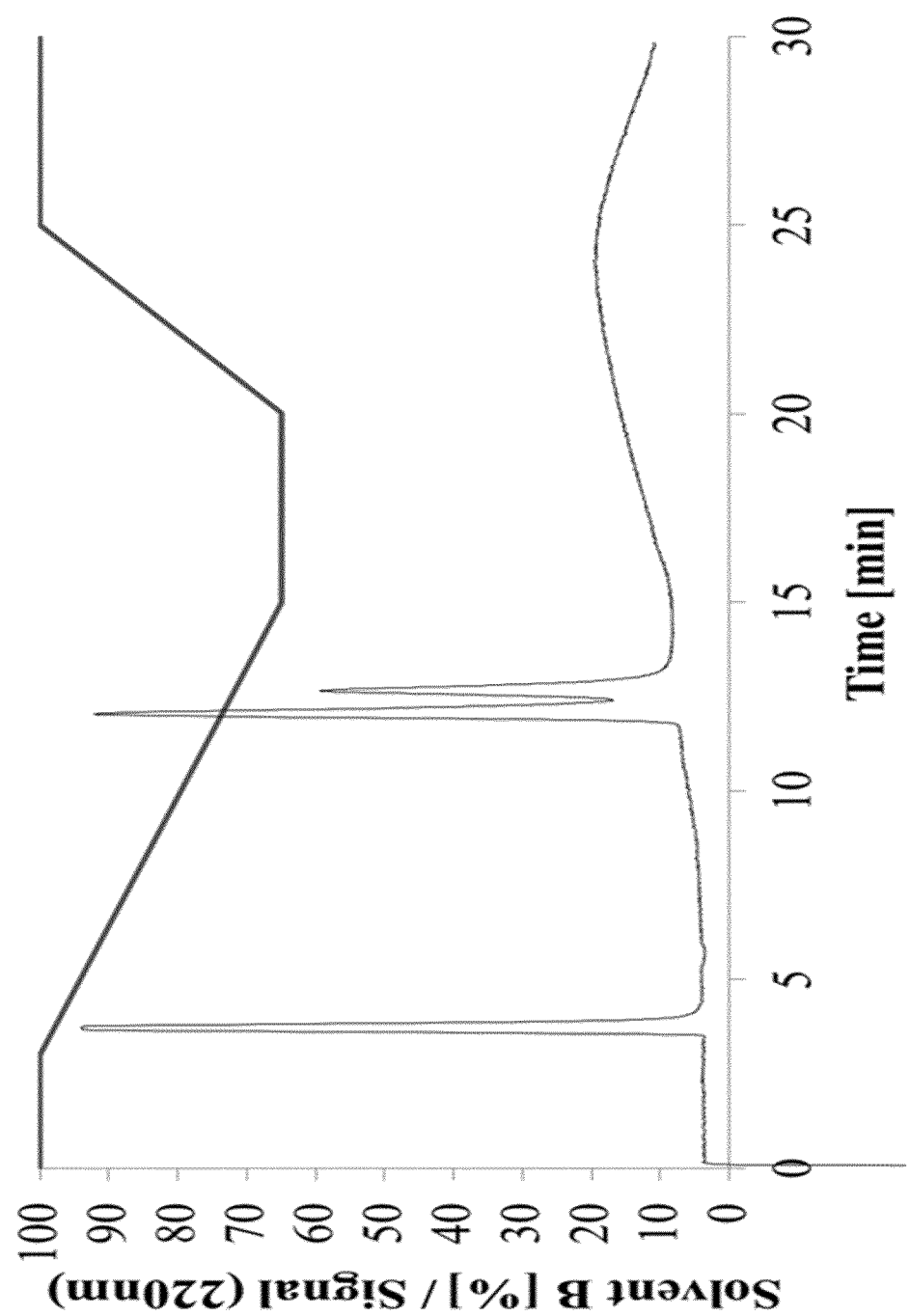
FIG. 2: HPLC-UV chromatogram of a thermally treated anserine nitrate salt with glucose.

D-Glucose (127.37 mmol, 2.8 eq) and sodium bisulfite (12.389 mmol, 0.28 eq) were suspended in methanol (38 mL) and glycerol (19 mL). After stirring for 30 min at 100° C., anserine nitrate salt (44.22 mmol, 1.0 eq, Bachem) and acetic acid (5.1 mL) were added and the resulting mixture was heated for 3.5 hours at 100° C. Reaction mass was then cooled down and diluted with water (38 mL). The mixture was purified by preparative liquid chromatography using Phenomenex Luna 5μHILIC 250×4.60 mm column with 5 mM $NH_4Ac$ buffer in water (solvent A) and acetonitrile (90%, solvent B), adjusted to a pH 5.8. The resulting chromatogram and the gradient are presented in FIG. 2. The first peak was identified as the nitrate salt while peak 2 is the desired 1-deoxy-D-fructosyl-N-β-alanyl-N-methyl-L-histidine and peak 3 corresponds to the unreacted anserine. Finally, 2.6 g 1-deoxy-D-fructosyl-N-β-alanyl-N-methyl-L-histidine were isolated (15%).

LC-MS (ESI$^-$): m/z 401.13 (100, [M-H]$^-$; $^1$H NMR (400 MHz, 300 K, Deuterium Oxide) δ 2.70-2.86 [m, 2H], 3.09 [dd, J=15.8, 8.3 Hz, 1H], 3.26 [dd, J=15.8, 5.0 Hz, 1H], 3.34-3.40 [m, 2H], 3.36 [m, 2H], 3.71-3.77 [m, 1H], 3.78-3.83 [m, 1H], 3.85 [s, 3H], 3.88-3.92 [m, 1H], 3.99-4.05 [m, 2H], 4.51 [dd, J=8.5, 5.5 Hz, 1H], 7.24 [s, 1H], 8.54 [s, 1H]; $^{13}$C NMR (100 MHz, 300 K, Deuterium Oxide) δ 28.77, 33.28, 35.87, 47.24, 55.96, 56.18, 66.85, 71.74, 72.14, 72.68, 98.18, 120.99, 133.96, 138.25, 174.55, 179.19.

EXAMPLE 5

Sensory Evaluation of Carnosine (β-alanyl-L-histidine) and Anserine (β-alanyl-N-methyl-L-histidine) in Model Broth The sensory tests were performed in a sensory panel room at 20-25° C. To avoid a retro-nasal aroma or taste impression, nose clips were used. The sensory panel consisted of 8 to 14 trained persons. The panel was trained to evaluate the taste of aqueous solutions (1 mL each) of the following standard taste compounds by using a triangle test: saccharose (50 mmol/L) and L-alanine (15 mmol/L), respectively, for sweet taste; lactic acid (20 mmol/L) for sour taste; NaCl (12 mmol/L) for salty taste; caffeine (1 mmol/L) and quinine hydrochloride (0.05 mmol/L), respectively, for bitter taste; sodium glutamate (8 mmol/L, pH 5.7) for umami taste; and tannin (0.05%) for astringency. The "white meaty" oral sensations was assessed in a model broth solution prepared from monosodium glutamate monohydrate (1.9 g/L), yeast extract (2.1 g/L), maltodextrin (6.375 g/L) and sodium chloride (2.9 g/L) in bottled water (pH 5.9).

The taste threshold concentration of β-alanyl-L-histidine was determined in the model broth using a three-alternative test with two blanks and one sample in ascending concentrations of β-alanyl-L-histidine. The taste threshold concentration was found to be 22'700 µmol/L (5.3 mg/g) for the thick-sour sensation and white-meaty oral impression.

The taste threshold concentration of β-alanyl-N-methyl-L-histidine can be determined in the same way as described above for the β-alanyl-L-histidine.

EXAMPLE 6

Sensory Evaluation of 1-deoxy-D-fructosyl-N-β-alanyl-L-histidine and 1-deoxy-D-fructosyl-N-β-alanyl-N-methyl-L-histidine in Model Broth The taste threshold concentration of 1-deoxy-D-fructosyl-N-β-alanyl-L-histidine was determined in model broth as described in Example 5 and was found to be 4'400 µmol/L (1.7 mg/g) for the thick-sour sensation and white-meaty oral impression. This taste threshold value is considerably lower than the 22'700 µmol/L (5.3 mg/g) threshold level determined for the corresponding β-alanyl-L-histidine under the same experimental model system (see Example 5). In fact, it corresponds to a lowering of the taste threshold concentration by a factor of about 5.

This result means that about a 5-time smaller amount of molecules of 1-deoxy-D-fructosyl-N-β-alanyl-L-histidine is required to impart a same corresponding taste impact of flavour and umami taste enhancement in a food product than with the corresponding β-alanyl-L-histidine under the same conditions.

A same result and similar quantitative reduction can be observed when testing and comparing the taste threshold values of 1-deoxy-D-fructosyl-N-β-alanyl-N-methyl-L-histidine in comparison with the corresponding anserine (β-alanyl-N-methyl-L-histidine).

EXAMPLE 7

Identification and Quantification of 1-deoxy-D-fructosyl-N-β-alanyl-L-histidine in Meat-bouillons Preparation of the Pot-au-feu bouillon: The ingredients (from local market) and their amounts are summarized in Table 1. Meat pieces were suspended in 5 L cold water. 22.5 g NaCl were added and the mixture was boiled. After 2 hours, the vegetable-cuts were added to the bouillon and the preparation was boiled for an additional hour. The mixture was filtered to remove solid parts.

TABLE 1

| Ingredients of the pot-au-feu | | | |
|---|---|---|---|
| Vegetables | | Meat | |
| Leek | 140 g | Flat shoulder | 624 g |
| Onions | 45 g | Round shoulder | 62 g |

TABLE 1-continued

| Ingredients of the pot-au-feu | | | |
|---|---|---|---|
| Vegetables | | Meat | |
| Celery | 108 g | Bone marrow | 180 g |
| Navets | 88 g | Knuckle of veal | 190 g |
| Clove | 0.35 g | Oxtail | 303 g |
| Carrots | 136 g | Flat rips | 251 g |

Preparation of the meat bouillon: Meat pieces were suspended in 5 L cold water (Table 1). 22.5 g NaCl were added and the mixture was boiled for 3 hours. The mixture was filtered to remove solid parts.

50 mL bouillons were spiked with a defined amount of $^{13}C_6$-labeled standards, applied on a Strata C18-E cartridge and eluted with water to reach an effective dilution of 1:10.

Quantification was done by stable isotopic dilution analysis using a HPLC-MS equipped with TSKgel-Amide 80 column (3 µm, 2 mm×150 mm from Tosoh Bioscience, Stuttgart, Germany) and the guard column TSKgel-Amide 80 (3 µm, 2 mm×10 mm from Tosoh Bioscience, Stuttgart, Germany). The eluent A was a mixture of acetonitrile with 1.0% formic acid and the eluent B was water with 1.0% formic acid. The injection volume was 3 µL. The flow rate was 0.2 mL/min. The solvent gradient started at 95% A from 0 to 5 min then 95-5% A from 5 to 15 min, 5% A for 10 min, 5-95% from 27 to 30 min. Table 2 summarizes MS conditions.

TABLE 2

| Mass transitions | | | | | |
|---|---|---|---|---|---|
| Substance | MW [Da] | Q1 → Q3 [m/z] | DP[a] | CE[b] | CXP[c] |
| 1-Deoxy-D-fructosyl-N-β-alanyl-L-histidine | 388 | 389 → 305 | 71 | 25 | 4 |

[a]Declustering Potential;
[b]Collision Energy;
[c]Cell Exit Potential

1-Deoxy-D-fructosyl-N-β-alanyl-L-histidine was found at 10 and 7 µmol/L in meat and pot-au-feu bouillons. This corresponds to a concentration of about 2.7 and 3.9 µg/g broth, respectively.

EXAMPLE 8

Seasoning Compositions

Chicken soups were prepared by dissolving 6 g chicken base powder (detailed recipe shown in Table 3) and 1 g monosodium glutamate in 500 mL hot water. 1-Deoxy-D-fructosyl-N-β-alanyl-L-histidine or alternatively 1-deoxy-D-fructosyl-N-β-alanyl-N-methyl-L-histidine was added at 2 g/L.

TABLE 3

| Composition of chicken base powder | |
|---|---|
| Ingredient | Quantity (%) |
| Chicken Meat powder | 30 |
| Starch | 1.52 |
| Flavors | 2.58 |
| Celery powder | 0.50 |
| Garlic powder | 0.90 |

TABLE 3-continued

| Composition of chicken base powder | |
|---|---|
| Ingredient | Quantity (%) |
| Chicken fat | 8.00 |
| Maltodextrine | 56.50 |
| Total | 100 |

The sensory evaluation was carried out by 12 panelists, previously screened for their sensory abilities. The panelists were asked to taste a set of 2 chicken soups, one containing no 1-deoxy-D-fructosyl-N-β-alanyl-L-histidine and one containing 1-deoxy-D-fructosyl-N-β-alanyl-L-histidine (2 g/L). If sensory differences were observed, the panelists were asked to describe them.

The sensory panel concluded that chicken soups with and without the 1-deoxy-D-fructosyl-N-β-alanyl-L-histidine were perceived as significantly different and the addition of 1-deoxy-D-fructosyl-N-β-alanyl-L-histidine significantly increased the boiled chicken and meaty flavours.

The same sensory evaluation was carried out with the chicken soup samples with and without containing 1-deoxy-D-fructosyl-N-β-alanyl-N-methyl-L-histidine at 2 g/L broth. The sensory panel concluded that chicken soups with and without the 1-deoxy-D-fructosyl-N-β-alanyl-N-methyl-L-histidine were perceived as significantly different and the addition of 1-deoxy-D-fructosyl-N-β-alanyl-N-methyl-L-histidine significantly increased the boiled chicken and meaty flavours.

EXAMPLE 9

Seasoning Compositions

Tomato soups were prepared by dissolving in 6 g tomato base powder (detailed recipe shown in the Table 4) in 500 mL hot water. 1-Deoxy-D-fructosyl-N-β-alanyl-L-histidine or alternatively 1-deoxy-D-fructosyl-N-β-alanyl-N-methyl-L-histidine was added at 2 g/L to the soups.

TABLE 4

| Composition of tomato soup powder | |
|---|---|
| Ingredient | Quantity (g) |
| Yeast extract | 0.036 |
| White Sugar | 0.348 |
| Flavors | 0.629 |
| Tomato powder | 0.03 |
| Wheat flour | 0.562 |
| Corn starch | 0.247 |
| Guar gum | 0.012 |
| Spices powder | 0.071 |
| Maltodextrine | 0.038 |
| Sunflower oil | 0.022 |
| Total | 2 |

The sensory panel concluded that tomato soups with and without the 1-deoxy-D-fructosyl-N-β-alanyl-L-histidine or 1-deoxy-D-fructosyl-N-β-alanyl-N-methyl-L-histidine were perceived as significantly different; and the addition of 1-deoxy-D-fructosyl-N-β-alanyl-L-histidine and alternatively 1-deoxy-D-fructosyl-N-β-alanyl-N-methyl-L-histidine increased significantly the savory, spicy notes of those soups.

The invention claimed is:

1. A composition comprising the compound of the general formula I,

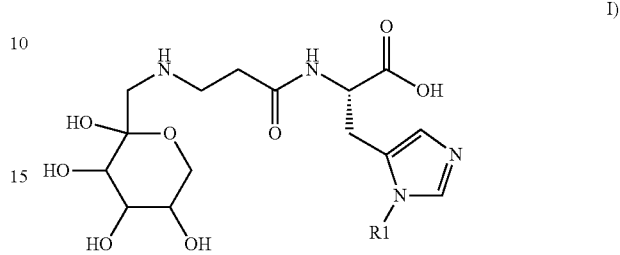

wherein R1 is selected from the group consisting of a hydrogen, a $C_1$, a $C_2$, a $C_3$, and a $C_4$ alkyl group, or a salt of the compound, the composition is selected from the group consisting of a culinary seasoning, a sauce or soup concentrate, and dry or wet pet-food product, and a final concentration of the compound in the composition is 1 mg/g to 3 mg/g.

2. The composition according to claim 1, wherein the composition is an extract from plant and/or meat material.

3. The composition according to claim 1, wherein the composition is the result of a flavor reaction.

4. A method for enhancing the flavor and/or umami taste of a culinary food product, the method comprising adding a compound of the general formula I,

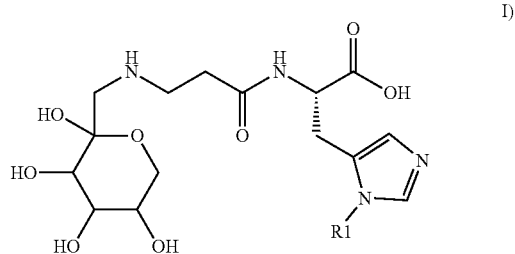

wherein R1 is selected from the group consisting of a hydrogen, a $C_1$, a $C_2$, a $C_3$, and a $C_4$ alkyl group, or a salt of the compound to the culinary food product, and a final concentration of the compound in the culinary food product is 1 mg/g 3 mg/g.

5. The composition of claim 1, wherein the final concentration of the compound in the composition is 1 mg/g to 2.5 mg/g.

6. The composition of claim 1, wherein the final concentration of the compound in the composition is 1 mg/g to 2.0 mg/g.

7. The method of claim 4, wherein the final concentration of the compound in the culinary food product is 1 mg/g to 2.5 mg/g.

8. The method of claim 4, wherein the final concentration of the compound in the culinary food product is 1 mg/g to 2.0 mg/g.

* * * * *